(12) United States Patent
Bassi

(10) Patent No.: US 8,535,950 B2
(45) Date of Patent: *Sep. 17, 2013

(54) USE OF PERFLUOROPOLYMER SUBMICROMETRIC LATEXES IN THE DETERMINATION OF MOLECULAR INTERACTIONS BY LASER LIGHT SCATTERING (LLS)

(75) Inventor: Mattia Bassi, Milan (IT)

(73) Assignee: Solvay Solexis S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/087,555

(22) Filed: Apr. 15, 2011

(65) Prior Publication Data

US 2011/0189795 A1 Aug. 4, 2011

Related U.S. Application Data

(63) Continuation of application No. 11/662,925, filed as application No. PCT/EP2005/010034 on Sep. 16, 2005, now Pat. No. 7,998,756.

(30) Foreign Application Priority Data

Mar. 15, 2007 (IT) ............... MI2004A1801

(51) Int. Cl.
*G01N 33/544* (2006.01)
*G01N 33/53* (2006.01)
*G01N 33/547* (2006.01)

(52) U.S. Cl.
USPC ............ 436/528; 435/7.5; 435/7.92; 436/532

(58) Field of Classification Search
None
See application file for complete search history.

(56) References Cited

U.S. PATENT DOCUMENTS

| | | | |
|---|---|---|---|
| 4,485,250 A | 11/1984 | Squire | |
| 4,703,018 A | 10/1987 | Craig et al. | |
| 4,745,165 A | 5/1988 | Arcella et al. | |
| 4,789,717 A | 12/1988 | Giannetti et al. | |
| 4,864,006 A | 9/1989 | Giannetti et al. | |
| 4,910,276 A | 3/1990 | Nakamura et al. | |
| 5,079,155 A | 1/1992 | Cox et al. | |
| 5,173,553 A | 12/1992 | Albano et al. | |
| 5,266,498 A | 11/1993 | Tarcha et al. | |
| 5,270,193 A | 12/1993 | Eveleigh | |
| 5,313,264 A | 5/1994 | Ivarsson et al. | |
| 5,374,563 A | 12/1994 | Maule | |
| 5,585,449 A | 12/1996 | Arcella et al. | |
| 5,690,907 A | 11/1997 | Lanza et al. | |
| 5,939,021 A | 8/1999 | Hansen et al. | |
| 6,180,415 B1 | 1/2001 | Schultz et al. | |
| 6,297,334 B1 | 10/2001 | Marchese et al. | |
| 6,413,786 B1 | 7/2002 | Hansen et al. | |
| 7,998,756 B2 * | 8/2011 | Bassi ........................ 436/528 |
| 2001/0023077 A1 | 9/2001 | Erb et al. | |
| 2004/0014060 A1 | 1/2004 | Hoheisel et al. | |
| 2004/0253744 A1 | 12/2004 | Rife et al. | |

FOREIGN PATENT DOCUMENTS

| | | |
|---|---|---|
| DE | 199 38 369 A1 | 3/2001 |
| EP | 0 633 257 | 4/1997 |
| EP | 0 250 766 | 9/1999 |
| EP | 1 300 684 A | 4/2003 |
| WO | WO 00/48023 | 8/2000 |

OTHER PUBLICATIONS

Hamola et al., "*Surface Plasmon resonance Sensors: review*", Sensor and Actuators B 54, 1999, p. 3-15.
Schuck., "*Use of surface Plasmon resonance to probe the equilibrium and dynamic aspects of interactions between biological micromolecules*", Annu. Rev. Biophys. Biomol. Struct., 1997, 26, pp. 541-566.
Giannetti et al., "*Polymerization of fluorinated monomers in perfluoropolyether microemulsions*", RICHMAC Magazine, La Chimica e I' Industria, 1997, pp. 22-29.
Angew. Chem. Int. Ed. 1988, 37, p. 2785.

* cited by examiner

*Primary Examiner* — Shafiqul Haq
(74) *Attorney, Agent, or Firm* — Arent Fox LLP

(57) ABSTRACT

Use of a latex of perfluorinated polymers having particles with an average diameter between 5 and 200 nm for determining the binding constant of two interacting molecular species by Laser Light Scattering (LLS), said polymeric particles comprising on the surface an amphiphilic non ionic surfactant, the same or a different surfactant ended with a receptor and a ligand interacting with the receptor.

11 Claims, 1 Drawing Sheet

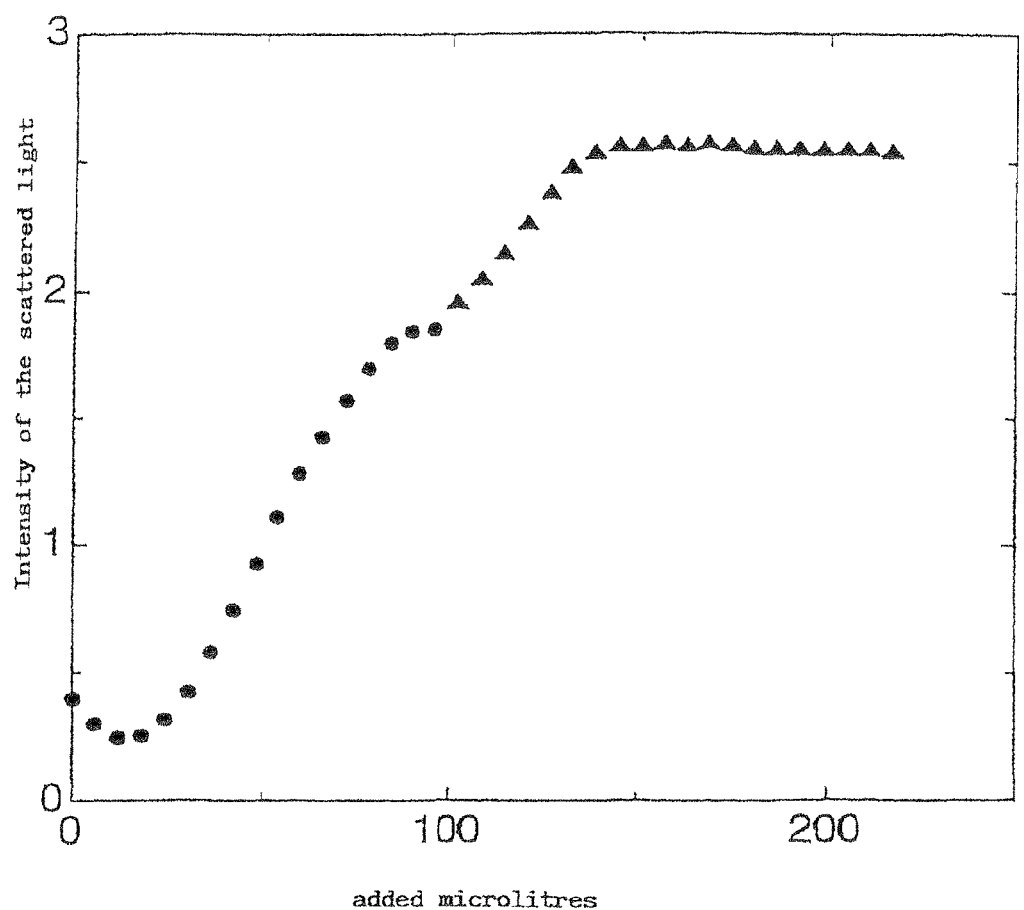

USE OF PERFLUOROPOLYMER SUBMICROMETRIC LATEXES IN THE DETERMINATION OF MOLECULAR INTERACTIONS BY LASER LIGHT SCATTERING (LLS)

CROSS REFERENCE TO RELATED APPLICATION

This application is a continuation of U.S. application patent No 11,662,925, filed Mar. 15, 2007, which is a National Phase of International Application No. PCT/EP2005/010034 filed on Sep. 16, 2005, which claims priority from Italy Application No. MI2004 A 001801. The disclosures of the prior applications are hereby incorporated by reference in their entirety.

The present invention relates to a simple and effective method for the quantitative determination of ligand interactions with receptors adsorbed on the particle surface by direct light scattering measurement.

More specifically the present invention relates to a method for the quantitative determination of ligand interactions with receptors wherein submicrometric polymeric particles, having a diameter between 5 and 200 nm, preferably having particle sizes between 40 and 80 nm, are used.

Several methods have been suggested in the prior art to determine interactions between ligands and receptors, i.e. the binding affinities of ligand-receptor reversible systems of chemical, biochemical or biological interest. A list of the main methods is reported in Angew. Chem. Int. Ed. 1998, 37, page 2785.

Said known methods generally comprise the receptor immobilization on a suitable flat surface and the measurement of the property variations, for example the optical ones, of said surface in contact with the ligands, said variations being induced by the formation of receptor-ligand couples.

One class of methods requires the ligand labelling in solution, i.e. the covalent ligand modification with fluorescent, luminescent or radioactive species. See for example patent application US 2004/0014060. However the ligand modification is a very complex and long operation and it can hardly be used in screening tests wherein a remarkable variety of ligands is used. Furthermore the method requires an additional removal operation from the system by washing out the free ligands, i.e. those which have not interacted with the receptors and which interfere with the measurement.

A further drawback of said method is that the ligand-receptor interaction can be influenced by the chemical modification of the ligand following the labelling.

Another class of methods simulating more effectively the receptor-ligand interactions, for example those occurring on a cell membrane surface, is that directly utilizing the variations induced on a surface by the bond formation in the receptor-ligand couple without modifying the ligand with labelling substances. An example of said method is the one using the BIAcore biosensor, marketed by Pharmacia Biosensor AB (Uppsala, Sweden) described for example in patents U.S. Pat. Nos. 5,313,264 and 5,374,563.

In this biosensor, based on the principle of the Surface Plasmon Resonance (SPR) (J. Homola et al. "Surface Plasmon Resonance Sensors: review", Sensor and Actuators B 54 (1999) 3-15), an evanescent optical wave couples with surface plasmons of thin layers (50 nm) of conductor materials as silver or gold, and generates a resonance phenomenon at specific angles. This allows to determine the refractive index variation of the layer adsorbed on the metal, for example a ligand-receptor couple. From this variation the binding constants between ligand and receptor are obtained.

Said method, even if it is very used in practice, is rather complicated and expensive and is not always suitable in the determination of the binding constants. See for example the publication "Use of surface plasmon resonance to probe the equilibrium and dynamic aspects of interactions between biological macromolecules", by Peter Schuck, Annu. Rev. Biophys. Biomol. Struct., 1997, 26; pages 541-66. The problems connected to the use of the BIAcore method for the binding constant determination depend on:
1) the ligand mass transport influencing the determination;
2) the steric hindrance of the ligand-receptor couple (bulk effect) and the distribution of the binding sites on the sensor, influencing the adsorption and desorption constants. Therefore, often, the association and dissociation constants obtained with this method differ of some orders of magnitude from those obtained by other methods;
3) the fact that the measurements are not taken under thermodynamic equilibrium conditions (kinetic approach).

The need was therefore felt to have available a method for the determination of interactions between ligands and receptors directly using the variations induced by the ligand-receptor interaction on a surface avoiding the ligand labelling and washing operations and able to act under thermodynamic equilibrium conditions, avoiding the drawbacks of the kinetic methods such as for example BIAcore.

BRIEF DESCRIPTION OF THE SEVERAL VIEWS OF THE DRAWING(S)

FIG. 1 is a graph showing measured intensity values as a function of the added solution volumes in microliters in accordance with aspects of the present invention.

It has been surprisingly and unexpectedly found that it is possible to overcome the above drawbacks with a quantitative optical method which allows to determine the binding affinities of molecular species in thermodynamic equilibrium by the method described hereinafter.

It is an object of the present invention the use of a colloidal aqueous suspension, or latex of perfluorinated polymers having particles with an average diameter between 5 and 200 nm, preferably between 40 and 80 nm, for determining the binding constant of two interacting molecular species by Laser Scattering Light (LLS), said polymeric particles comprising on the surface an amphiphilic non-ionic surfactant, a surfactant ended with a receptor and a ligand interacting with the receptor.

The surfactant of the amphiphilic non ionic surfactant and of the surfactant ended with a receptor can be the same or different.

More specifically the use comprises the following steps:
a) addition to a colloidal aqueous suspension or latex of particles having an average diameter between 5 and 200 nm, preferably between 40 and 80 nm, formed of a perfluorinated, semicrystalline or amorphous polymer, of a sequence of known volumes of an aqueous solution of a mixture containing from 50% to 99.5% by weight of an amphiphylic non ionic surfactant and from 0.5 to 50% by weight of a surfactant ended with a receptor, measuring after each addition the intensity of the scattered light by the suspension by Laser Scattering Light (LLS) and reporting it on a diagram in function of the progressively added solution volume, until reaching an asymptotic value ($I_r$);
b) addition to the suspension obtained in step a) of a sequence of known volumes of a ligand aqueous solution, measuring after each addition the intensity of the scattered light by the suspension by Laser Scattering Light (LLS) its reporting on a diagram in function of the progressively added solution volume (expressed as molar concentration $[T_0]$), until reaching an asymptotic value and fitting the scattered light intensity data (I) in function of the ligand additions ($[T_0]$) with formula (1) to obtain the receptor-ligand binding constant (K), wherein formula (1) is:

$$I = I_0 \left( \sqrt{\frac{I_r}{I_0}} + \frac{m_l(n_l^2 - n_w^2)([T_0] + K^{-1} + [S_0] - \sqrt{([T_0] + K^{-1} + [S_0])^2 - 4[T_0][S_0]})}{2\rho_l(n_p^2 - n_w^2)\phi_p} \right)^2$$

where $I_0$ is the intensity of light scattered by uncovered particles, $I_r$ is the intensity of light scattered by particles covered by receptors (asymptotic value)

$n_w$ s the solvent refractive index, $n_p$ is the refractive index of uncovered particles, $n_l$ is the refractive index of ligands, $\phi_p$ is the fraction of suspension volume occupied by the particles, $\rho_l$ is the density of pure ligand., $m_l$ is the molecular weight of ligand molecule, $[S_0]$ is the total molar concentration of ligand-receptor interaction sites, $[T_0]$ is the total molar concentration of ligands added to the suspension, K is the binding constant, $[S_0]$ and K being the only two parameters to be obtained by the fitting.

In particular, in step a) it is preferred to use a colloidal aqueous suspension or latex containing from 0.05% to 5%, preferably from 0.1 to 1% by weight, of spheroidal particles of an amorphous or semicrystalline perfluorinated polymer.

The fitting of the scattered light intensity data I due to binding of ligands to adsorbed receptors, in function of the ligand additions ($[T_0]$) is carried out by considering the Rayleigh model for the intensity of light scattered by particles much smaller than the wavelength (H. C. van de Hulst "Light Scattering by Small Particles", Dover Publications Inc., New York, 1981) together with the equation for the Langmuir isotherm (see, for example, Paul C. Hiemenez "Principles of Colloid and Surface Chemestry", Marcel Dekker, New York, 1997, pages 287-298).

The latex perfluoropolymers are selected, for example, from:

1) tetrafluoroethylene homopolymer (PTFE), or semicrystalline tetrafluoroethylene (TFE) copolymers;

2) amorphous TFE copolymers;

3) amorphous homopolymers of perfluorinated dioxole rings.

Preferably the latex perfluoropolymers are selected from:

1) semicrystalline tetrafluoroethylene (TFE) copolymers containing from 0.5% up to about 10% by moles, the maximum limit being such that the copolymer is semi-crystalline, of one or more fluorinated monomers different from TFE, such as for example perfluoroalkyl-vinyl-ethers (PAVE), perfluorodioxoles, hexafluoropropene (HFP);

2) amorphous TFE copolymers with other fluorinated monomers, as for example perfluoroalkyl-vinylethers (PAVE), perfluorodioxoles of formula

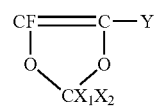

wherein Y is equal to F or to $OR_f$ wherein R is a perfluoroalkyl having from 1 to 5 carbon atoms; preferably Y is equal to $OR_f$; $X_1$ and $X_2$, equal to or different from each other, are —F or —$CF_3$; preferably in formula (I) $X_1$, $X_2$ are —F; $R_f$ is preferably —$CF_3$, —$C_2F_5$, or —$C_3F_7$; more preferably the fluorodioxoles of formula (I) are those wherein Y is equal to $OR_f$ wherein $R_f$ is —$CF_3$ and $X_1$, $X_2$ are —F (i.e. 2,2,4-trifluoro-5-trifluoromethoxy-1,3-dioxole (TTD)) (see for example EP 633 257); hexafluoropropene (HFP); perfluorooxyalkyl vinylethers, optionally containing "cure-site" monomers containing bromine or iodine atoms (see for example U.S. Pat. No. 4,745,165) or iodine or bromine atoms in end position in the polymeric chain (see for example U.S. Pat. No. 5,173,553); bisolefins having general formula:

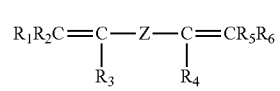

wherein:

$R_1, R_2, R_3, R_4, R_5, R_6$, equal to or different from each other, are H or $C_1$-$C_5$ alkyls, Z is a linear or branched $C_1$-$C_{18}$ alkylene or cycloalkylene radical, optionally containing oxygen atoms, preferably at least partially fluorinated, or a (per) fluoropolyoxyalkylene radical (see for example U.S. Pat. No. 5,585,449);

3) amorphous homopolymers of a perfluorodioxole of formula (I) as above.

In class 2), as comonomer of TFE, alternatively to the perfluorodioxole of formula (I), dioxole rings can be used, deriving from the cyclization of bis-olefinic monomers containing oxygen atoms described in U.S. Pat. No. 4,910,276. As Example the following monomers can be cited:

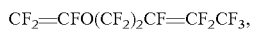

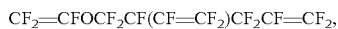

More preferably the latex. perfluoropolymer is an amorphous perfluoropolymer. In particular, the amorphous TFE copolymers containing from 20% to 50% by moles of one or more perfluoroalkylvinyl-ethers are preferred, preferably selected from perfluoro-methylvinylether, perfluoroethylvinylether, perfluoropropyl-vinylether. Another class of preferred copolymers is the one including amorphous copolymers of TFE containing from 20% to 80% by moles of the perfluorodioxole of formula (I), in particular TTD, as above reported.

Aqueous latexes containing perfluoropolymer particles having average particle sizes indicated in step a) can be prepared by monomer polymerization in aqueous emulsion in the presence of a microemulsion of (per)fluoropolyoxy-alkylenes, according to what described in patents U.S. Pat. Nos. 4,864,006, 4,789,717, EP 250,766, U.S. Pat. No. 6,297,334 and in publication "Polymerization of fluorinated monomers in perfluoropolyether microemulsion", Giannett E., Chittofrati A., Sanguineti A., La chimica e l'industria, Ottobre 1997, RICHMAC Magazine, herein incorporated by reference.

As amphiphilic non-ionic surfactants those generating a self assembled monolayer on the latex particles are used. The obtainment of said monolayer can be present achieved by carrying out step a) of the method of the invention by using only the amphiphilic non-ionic surfactant, without the addition of the surfactant ended with the receptor, and observing the reaching of an asymptotic value of the diagram.

Furthermore said amphiphilic non-ionic surfactants must not have specific interactions, i.e. they must not form a bond with the ligand to be analyzed. The absence of such interaction can be verified by carrying out step a) of the method according to the invention by using only the amphiphilic non-ionic surfactant, without the addition of the surfactant ended with the receptor, then carrying out step b) and verifying that there are no variations of the scattered light intensity.

As amphiphilic non-ionic surfactants usable in the present invention it can be mentioned for example:

a) non ionic compounds having structure $$CH_3-(CH_2)_n-(OCH_2CH_2)_mOH$$

wherein n and in are integers, 6<n<18 and 3<m<12 for example the commercial compound Brij 56 (Fluxa, cas. No. 9004-95-9) wherein n=15 and m, as average, is around 10;

b) alkyl glycosides with the following structure $$RO-(CH_2)_n-CH_3$$

wherein n is an integer, 6<n<12 and R is a glucose or maltose residue, for example the commercial compound n-dodecyl-beta-D-maltoside by Aldrich.

The surfactants ended with a receptor are prepared by reaction of the above described surfactants with receptors according to known processes of the prior art.

The receptor-ligand couple is defined as a molecule couple, for example proteins, nucleic acids, glycoproteins, carbohydrates, hormones, having an affinity capable to set a more or less stable bond. In particular antibody/antigen, enzyme/inhibitor, carbohydrate/carbohydrate, protein/DNA, DNA/DNA, peptide/peptide, can be mentioned.

In steps a) and b) the measurements of the scattered light intensities are carried out under thermodynamic equilibrium conditions, i.e. alternating the additions with periods of time, generally 4-6 minutes, to stabilize the suspension.

It has been found that the invention system rapidly reaches the thermodynamic equilibrium. Therefore the measurements carried out are independent from the absorption desorption kinetics and therefore are not influenced by the mass transport.

The geometry of the colloidal system with submicrometric particles makes available a larger surface in comparison with the systems utilizing flat surfaces, a solution volume being fixed. The surface available for the ligand for millilitre of latex is generally between 500 and 2000 cm$^2$.

The method of the present invention allows to detect up to 3 micrograms of material per millilitre, corresponding to a sensitivity limit on the adsorbed mass for surface of 0.04 nanograms/mm$^2$ which is of the order of the most sensitive techniques of the prior art.

It is surprising and unexpected that the Light Scattering (LS) has resulted effective to identify and measure interactions between receptors and ligands according to the method of the present invention. In fact the interaction of ligands with receptors in diluted solutions is not determinable by LS. The use of submicrometric particles capable to support a multiplicity of receptors allows to use the LS to measure the ligand-receptor interaction.

It is worth while noting that the presence of interactions between a ligand and more receptors supported on different particles (indicated herein as polyvalent interactions) make inapplicable the method of the present invention. In case of several polyvalent interactions the latex can coagulate. The existence of said polyvalent interactions can be verified by measuring the particle size during steps a) and b) by the Dymanic Laser Light Scattering (DLLS) technique. The dynamic DLLS method is based on the registration of a autocorrelation curve correlating the scattering intensity and the relaxation time of the scattering particles. In this way it is thus possible to draw a relaxation rate Γ, which is proportional to the scattering coefficient D of the scattering species:

$$\Gamma = D*q^2$$

wherein q represents the wave vector having the following equation:

$$q = (4\pi n_D/\lambda)\sin(\theta/2)$$

wherein $n_D$ is the medium refractive index, λ is the wave length and θ is the prefixed scattering angle at which the measurements are carried out.

The scattering coefficient D is also correlated to the diameter of the scattering articles through the Stokes-Einstein equation:

$$D = kT/3\pi\eta\phi$$

wherein K is the Boltzmann constant, T the temperature, η the viscosity of the suspension (latex) and φ the diameter of the scattering articles. Therefore from this equation the particle diameter can be calculated. In the absence of polyvalent interactions, the polymeric particle diameter remains substantially constant. The diameter variation is due to the monomolecular layer formed by the surfactant, by the receptor and by the ligand.

The diameter variation control is particularly important when there is no coagulation even in the presence of polyvalent interactions. In this case the measurements are not significant of the ligand-receptor interactions. Therefore the interactions between receptor and ligand must not be polyvalent interactions. In general the diameter variation for not polyvalent interactions is of the order of about some nanometers (e.g. 1-10 nm) per support polymer particles having a diameter of about 40 nm.

The polyvalent interactions are present when, by using support polymer particles having a diameter of about 40 nm, particles of about 80 nm are found.

Some Examples are given for illustrative but not limitative purposes of the present invention.

EXAMPLES

Example 1

Measurement he Binding Constant between Vancomycin Hydrochloride Hydrate (Ligand) and the Peptide Sequence L-Lys-D-Ala-D-Ala (Receptor)

Step a)

To a colloidal aqueous suspension containing 0.1% by weight of particles having an average diameter of 78 nm, constituted of a TFE copolymer containing 40% by moles of perfluoromethylvinylether, it was added a 10 millimolar aqueous solution of a mixture containing 99% by weight of n-dodecyl-beta-D-maltoside and 1% by weight of the non ionic surfactant Brij 56 ended with the peptide sequence L-Lys-D-Ala-D-Ala, sequence characteristic of the bacterium cellular wall, each in 6 microlitre portions, at intervals of 5 min.

After each addition the mixture was stirred for 30 seconds and allowed to balance for 1 minute, and the scattering light intensity was measured by using a 5 milliWatt He—Ne laser and a photomultiplier to convert the scattered light into an electric signal.

The light intensity was recorded for 10 seconds for consecutive six times then selecting the lowest value to minimize the noise due to the powder possibly present in the sample.

The measured intensity values (spots in FIG. 1) are represented by a diagram in function of the added solution volumes obtaining the curve reported in FIG. 1.

The progressive particle covering from the used mixture is noticeable from the variation of the scattered light intensity. The complete coating is clearly shown by the achievement of an asymptotic value of the scattered light intensity.

Step b)

To the suspension obtained in a), when the asymptotic value is reached, a 0.4 millimole aqueous solution of Vancomycin hydrochloride hydrate (marketed by Aldrich, cas. No. 861987) is added, each in 6 microlitre portions, at intervals of 5 minutes.

After each addition the mixture was stirred for 30 seconds and allowed to balance for 1 minute, and the scattered light intensity was measured as in step a).

The measured intensity values (triangles in FIG. 1) are represented by a diagram in function of the solution volumes and added to the curve of the diagram of step a).

The formation of the Vancomycin/L-Lys-D-Ala-D-Ala couples is revealed from the increase of the scattered light intensity until reaching an asymptotic value indicating the saturation of the receptor sites with Vancomycin.

By fitting to the scattered light intensity data, in function of the Vancomycin additions, the Langmuir absorption formula, the receptor-ligand binding constant is obtained.

The obtained binding constant is $1.5 \times 10^6$ moles$^{-1}$.

To verify the absence of aggregation processes, it was continuously controlled, by using the DLLS technique, that the submicrometric particle diameter substantially remained constant.

Example 2

The Example 1 was repeated but by using an acqueous colloidal suspension at 0.1% of particles having an average diameter of 40 nm, constituted of a TFE copolymer containing 30% by moles of 2,2,4-trifluoro-5-trifluoromethoxy-1,3-dioxole (TTD).

In step a) the same mixture of the Example 1 was added in 12 microlitre portions.

In step b) a 0.9 millimolar mixture of Vancomycin was added in 6 microlitre portions.

The obtained binding constant is $1.1 \times 10^6$ moles$^{-1}$.

What is claimed is:

1. A method for determining the binding constant of two interacting molecular species by Laser Light Scattering (LLS) comprising the steps of:

providing a colloidal aqueous suspension of particles containing perfluoropolymer or a latex suspension of particles containing perfluoropolymer with an average diameter between 5 and 200 nm;

measuring the intensity, $l_0$, of the light scattered by the colloidal aqueous suspension or latex;

sequentially adding to the colloidal aqueous suspension of particles or the latex suspention of particles, an aqueous solution of a mixture of an amphiphilic nonionic surfactant and a surfactant ended with a receptor to form a first mixture comprising perfluoropolymer particles that comprise on their surface an amphiphilic nonionic surfactant and a surfactant ended with a receptor;

measuring the intensity of the light, $l_r$, scattered by the first mixture by LLS after each addition of the aqueous solution to the colloidal aqueous suspension of particles or the latex suspension of particles;

repeating the addinq of an aqueous solution of a mixture of amphiphylic nonionic surfactant and surfactant ended with a receptor step and the measuring of the intensity, $l_r$, step until reaching an asymptotic value of intensity;

sequentially adding an aqueous solution of a ligand to the first mixture to form a second mixture comprising perfluoropolymer particles that comprise on their surface an amphiphilic nonionic surfactant, a surfactant ended with a receptor and a ligand having interacted with the receptor;

measuring the intensity of the light, l, scattered by the second mixture by LLS after each addition of the aqueous solution of the liqand to the first mixture;

repeating the adding of a ligand aqueous solution step and the measuring of the intensity, l, step until reaching an asymptotic value of intensity;

correlating the measured light intensity of the first mixture and the second mixture with the ligand solution additions; and determining the binding constant of two interacting molecular species based on the correlation, wherein the two interacting molecular species are the surfactant ended with the receptor and the ligand for the receptor, wherein the amphiphilic nonionic surfactant and the surfactant ended with a receptor can be the same or different surfactant, and wherein the wavelength of the laser light is greater than the average diameter of the particle.

2. The method according to claim 1, further comprising the steps of:

fitting the scattered light intensity, I, data as a function of the ligand solution additions with formula (1) to obtain the receptor-ligand binding constant, wherein formula (1) is:

$$I = I_0 \left( \sqrt{\frac{I_r}{I_0}} + \frac{m_l(n_l^2 - n_w^2)([T_0] + K^{-1} + [S_0] - \sqrt{([T_0] + K^{-1} + [S_0])^2 - 4[T_0][S_0]})}{2\rho_l(n_p^2 - n_w^2)\phi_p} \right)$$

where $l_0$ is the intensity of light scattered by uncovered particles, $l_r$ is the intensity of light scattered by particles covered by receptors, $n_w$ is the solvent refractive index, $n_p$ is the refractive index of uncovered particles, $n_l$ is the refractive index of ligands, Φp is the fraction of suspension volume occupied by the particles,
ρ₁ is the density of pure ligand,
m₁ is the molecular weight of ligand molecule,
[S₀] is the total molar concentration of ligand-receptor interaction sites,
[T₀] is the total molar concentration of ligands added to the suspension, and
K is the binding constant,
wherein the pefluoropolymer comprises amorphours or semicrystalline perluorinated polymers.

3. The method according to claim 2, wherein the colloidal aqueous suspension of particles or the latex suspension of particles comprises from 0.05% to 5% by weight of spheroidal amorphous or semicrystalline perfluoropolymer.

4. The method according to claim 1, wherein the perfluoropolymer is selected from the group consisting of:
1) tetrafluoroethylene homopolymer (PTFE), or semicrystalline tetrafluoroethylene (TFE) copolymers;
2) amorphous TFE copolymers; and
3) amorphous homopolymers of perfluorinated dioxole rings.

5. The method according to claim 4, wherein the perfluoropolymer is selected from the group consisting of:
1) semicrystalline tetrafluoroethylene (TFE) copolymers containing from 0.5% up to about 10% by moles, the maximum limit being such that the copolymer is semicrystalline, of one or more fluorinated monomers different from TFE selected from the group consisting of perfluoro-alkyl-vinylethers (PAVE), perfluorodioxoles, and hexafluoropropene (HFP);
2) amorphous TFE copolymers with other fluorinated monomers selected from the group consisting of perfluoroalkyl-vinylethers (PAVE), perfluorodioxoles of formula

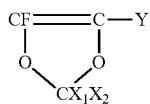

(I)

wherein Y is equal to F or to OR$_f$ wherein R$_f$ is a perfluoroalkyl having from 1 to 5 carbon atoms; X$_1$ and X$_2$, equal to or different from each other, are —F or —CF$_3$; hexafluoropropene (HFP); perfluorooxyalkyl vinylethers, optionally containing "cure-site" monomers containing bromine or iodine atoms or iodine or bromine atoms in end position in the polymeric chain; bis-olefins having general formula:

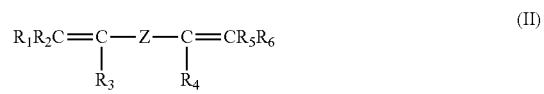

(II)

wherein:
R$_1$, R$_2$, R$_3$, R$_4$, R$_5$, R$_6$, equal to or different from each other, are H or C$_1$-C$_5$ alkyls, Z is a linear or branched C$_1$-C$_{18}$ alkylene or cycloalkylene radical, optionally containing oxygen atoms or a (per)fluoropolyoxyalkylene radical; and
3) amorphous homopolymers of a perfluorodioxole of formula (I) as above.

6. The method according to claim 5, wherein the TFE comonomer of class 2) is a dioxole ring that is derived from the cyclization of bis-olefinic monomers containing oxygen atoms, substituted with the perfluorodioxole of formula (I).

7. The method according to claim 4, wherein the perfluoropolymer is an amorphous perfluoropolymer.

8. The method according to claim 7, wherein the perfluoropolymer is an amorphous TFE copolymer containing from 20% to 50% by moles of one or more perfluoroalkylvinylethers.

9. The method according to claim 5, wherein the perfluoropolymer is an amorphous copolymer of TFE containing from 20% to 80% by moles of the perfluorodioxole of formula (I).

10. The method according to claim 1, wherein the aqueous solution sequentially added to the colloidal aqueous suspension of particles or the latex suspension of particles contains from 50% to 99.5% by weight of the amphiphilic nonionic surfactant.

11. The method according to claim 1, wherein the aqueous solution sequentially added to the colloidal aqueous suspension of particles or the latex suspension of particles contains from 0.5 to 50% by weight of the surfactant ended with the receptor.

* * * * *